United States Patent
Oosake

(10) Patent No.: US 11,222,243 B2
(45) Date of Patent: Jan. 11, 2022

(54) MEDICAL IMAGE PROCESSING DEVICE, MEDICAL IMAGE PROCESSING METHOD, AND MEDICAL IMAGE PROCESSING PROGRAM

(71) Applicant: FUJIFILM Corporation, Tokyo (JP)

(72) Inventor: Masaaki Oosake, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 39 days.

(21) Appl. No.: 16/795,541

(22) Filed: Feb. 19, 2020

(65) Prior Publication Data

US 2020/0193236 A1 Jun. 18, 2020

Related U.S. Application Data

(63) Continuation of application No. PCT/JP2018/026945, filed on Jul. 18, 2018.

(30) Foreign Application Priority Data

Sep. 15, 2017 (JP) .............................. JP2017-177491

(51) Int. Cl.
G06K 9/62 (2006.01)
G06T 7/70 (2017.01)
G06T 7/00 (2017.01)

(52) U.S. Cl.
CPC .......... *G06K 9/6262* (2013.01); *G06T 7/0012* (2013.01); *G06T 7/70* (2017.01);
(Continued)

(58) Field of Classification Search
CPC .... G06K 9/6262; G06K 2209/05; G06T 7/70; G06T 7/0012; G06T 2207/20084;
(Continued)

(56) References Cited

U.S. PATENT DOCUMENTS

2006/0274928 A1* 12/2006 Collins ................ A61B 6/5247
382/132
2009/0099862 A1* 4/2009 Fireman ........... G06Q 10/06375
705/2
(Continued)

FOREIGN PATENT DOCUMENTS

WO 2010050333 5/2010
WO 2017055412 4/2017

OTHER PUBLICATIONS

Alex Krizhevsky, et al., "ImageNet Classification with Deep Convolutional Neural Networks", Communications of the ACM, May 2017, pp. 1-9.
(Continued)

*Primary Examiner* — Vu Le
*Assistant Examiner* — Julius Chai
(74) *Attorney, Agent, or Firm* — JCIPRNET

(57) ABSTRACT

A medical image processing device having a processor configured to: acquire a medical image including an image of a subject; perform a first recognition of the medical image using a first recognizer; determine a confidence level for a recognition result of a first recognition by the first recognition; and perform a second recognition of the medical image using a second recognizer according to the confidence level for the recognition result of the first recognition, the second recognition having higher recognition accuracy than the first recognition.

18 Claims, 7 Drawing Sheets

(52) U.S. Cl.
CPC ............... *G06K 2209/05* (2013.01); *G06T 2207/20084* (2013.01); *G06T 2207/30096* (2013.01)

(58) Field of Classification Search
CPC . G06T 2207/30096; G06T 2207/10016; G06T 2207/10068; G16H 50/20
See application file for complete search history.

(56) References Cited

U.S. PATENT DOCUMENTS

2018/0247107 A1* 8/2018 Murthy ............... G06K 9/4628
2018/0365834 A1* 12/2018 Li ........................ G06K 9/66

OTHER PUBLICATIONS

Karen Simonyan, et al., "Very Deep Convolutional Networks For Large-Scale Image Recognition", Conference paper at ICLR 2015, Apr. 10, 2015, pp. 1-14.

Masayoshi Yamada, et al., "Development of real-time endoscopic image automatic analysis system for colorectal cancer and precancerous lesion detection using artificial intelligence system based on morphological information quantification", Japanese Journal of Gastroenterology, Sep. 2017, with English translation thereof, pp. 1-2.

"International Search Report (Form PCT/ISA/210) of PCT/JP2018/026945," dated Oct. 16, 2018, with English translation thereof, pp. 1-3.

"Written Opinion of the International Searching Authority (Form PCT/ISA/237) of PCT/JP2018/026945," dated Oct. 16, 2018, with English translation thereof, pp. 1-6.

* cited by examiner

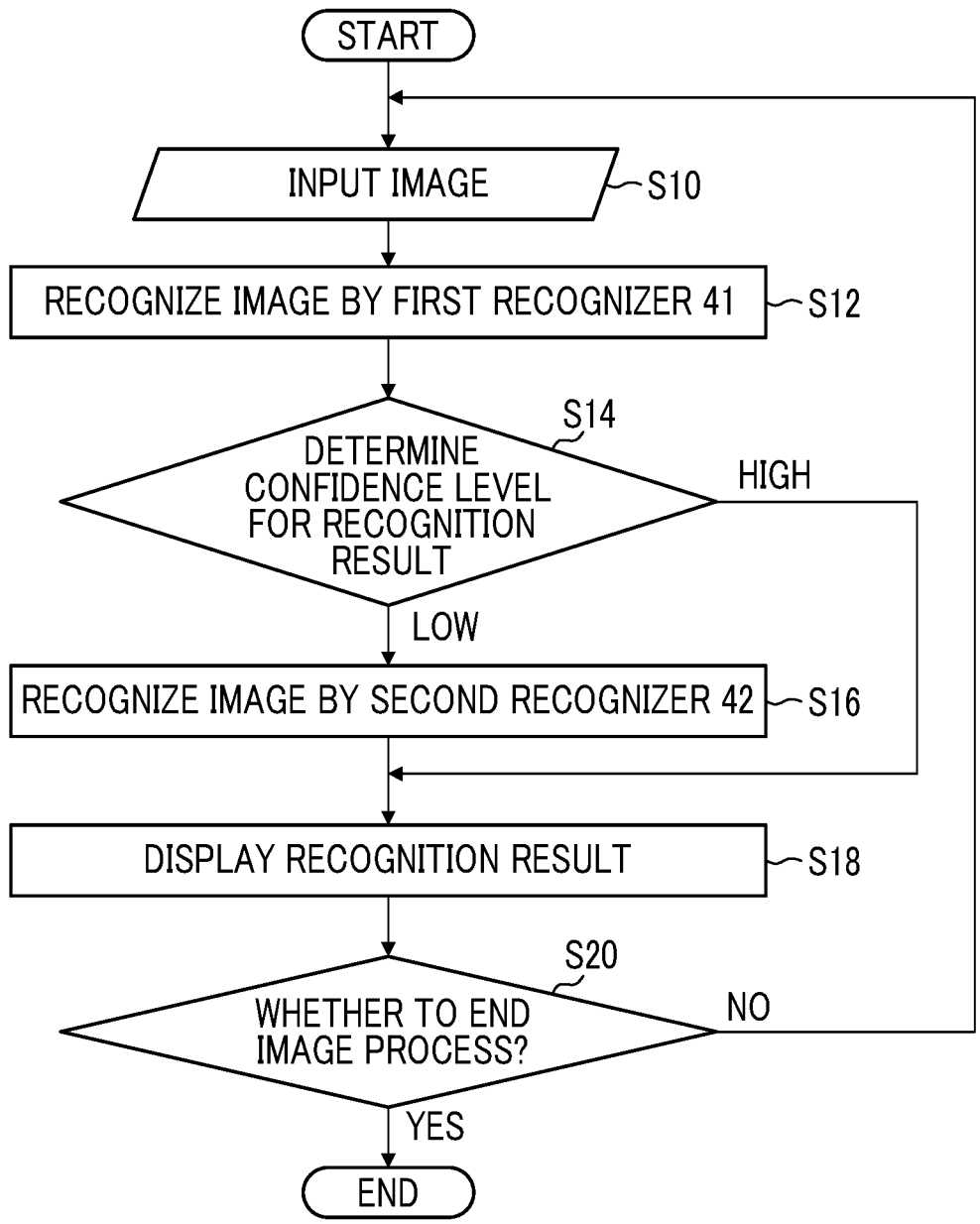

MEDICAL IMAGE PROCESSING DEVICE, MEDICAL IMAGE PROCESSING METHOD, AND MEDICAL IMAGE PROCESSING PROGRAM

CROSS-REFERENCE TO RELATED APPLICATIONS

This application is a Continuation of PCT International Application No. PCT/JP2018/026945 filed on Jul. 18, 2018, which claims priority under 35 U.S.C § 119(a) to Japanese Patent Application No. 2017-177491 filed on Sep. 15, 2017. Each of the above application(s) is hereby expressly incorporated by reference, in its entirety, into the present application.

BACKGROUND OF THE INVENTION

1. Field of the Invention

The invention relates to a medical image processing device, a medical image processing method, and a non-transitory computer readable medium for storing a medical image processing program, and more particularly relates to a technique for performing a recognition process of a medical image by using a recognizer.

2. Description of the Related Art

In the medical field, inspection using an endoscope system is performed. In recent years, a system of performing recognition of a lesion included in an image by image analysis has been known. For example, a convolutional neural network (CNN) which calculates a feature quantity from an image by learning to perform an image recognition process is known (A. Krizhevsky, I. Sutskever, and G Hinton. ImageNet classification with deep convolutional neural networks. In NIPS, 2012).

It is known that the CNN has a multiple layer structure including convolutional layers that perform convolutional operation using images and filters, and the recognition accuracy of the image is improved by the number of layers (K Simonyan, A Zisserman. Very Deep Convolutional Networks for Large-Scale Image Recognition. arXiv preprint arXiv: 1409.1556).

In the related art, as this type of information processing devices, a device which outputs, as an estimation value, a probability that an image to be recognized belongs to each class among a plurality of classes from the feature quantity obtained by image analysis, recognizes the class to which the image belongs on the basis of the estimation value, and calculates a confidence level for the recognition result using the estimation value of each class has been proposed (WO2010/050333).

For example, the information processing device disclosed in WO2010/050333 performs image analysis on a medical image, classifies the medical image into any of three classes of an imaging site (chest, abdomen, leg), and calculates a confidence level for the classification result (recognition result).

The information processing device disclosed in WO2010/050333 determines whether the confidence level is high or low on the basis of the value of the calculated confidence level, and in a case where it is determined that the confidence level is low, the information processing device causes display means to display warning information for warning that the confidence level is low together with the recognition result of the class.

SUMMARY OF THE INVENTION

As typified by an endoscope device, in some cases, it is required to recognize the position and type of a lesion from images and display the recognition result in real time. In a case where real time display is required, the image recognition process by a recognizer has to be performed at high speed.

However, there is a problem in that the recognition accuracy of the image becomes lowered in the recognizer which performs the image recognition process at high speed. For example, in case of the CNN, the number of layers of the multiple layer structure is required to be reduced for speeding up, but there is a problem in that the recognition accuracy of the image becomes lowered. Meanwhile, in a case where the number of layers of the layer structure is increased to improve the recognition accuracy of the image, there is a problem in that the amount of calculation is increased and the operation load on the recognizer is increased so that the recognition process is delayed.

The information processing device disclosed in WO2010/050333 recognizes the class to which the medical image belongs by the recognizer to display the recognition result of the class, and calculates the confidence level for the recognition result to display the warning information in a case where the confidence level is low.

Accordingly, in the information processing device disclosed in WO2010/050333, in a case where the recognizer which performs the image recognition process at high speed (recognizer with low recognition accuracy of the image) is applied, there is a problem in that the confidence level for the recognition result becomes lowered and the warning information is frequently displayed.

Meanwhile, in the information processing device disclosed in WO2010/050333, in a case where the recognizer which performs the image recognition process at low speed (recognizer with high recognition accuracy of the image) is applied, the confidence level for the recognition result becomes increased, but there is a problem in that the operation load is increased and the recognition result cannot be displayed in real time.

The invention has been made in view of such circumstances, and an object of the invention is to provide a medical image processing device, a medical image processing method, and a medical image processing program which can speed up an image recognition process and improve recognition accuracy.

In order to achieve the above-described object, a medical image processing device according to an aspect of the invention comprises a medical image acquisition unit that acquires a medical image including an image of a subject; a first recognizer that performs recognition of the medical image; a second recognizer that performs recognition of the medical image and has higher recognition accuracy than the first recognizer; a recognition confidence level determination device that determines a confidence level for a recognition result by the first recognizer; and a control unit that executes a recognition process of the medical image by the second recognizer according to a determination result of the recognition confidence level determination device.

According to the aspect of the invention, it is possible to speed up the image recognition process by using the first recognizer which performs recognition of the medical image and has a low load of the image recognition process, and in a case where the confidence level for the recognition result by the first recognizer is low, it is possible to improve the recognition accuracy by using the second recognizer having higher recognition accuracy of the image (high load of the recognition process).

In the medical image processing device according another aspect of the invention, each of the first recognizer and the second recognizer may have a layer structure.

In the medical image processing device according still another aspect of the invention, the number of layers constituting the layer structure of the second recognizer may be greater than the number of layers constituting the layer structure of the first recognizer. Since the number of layers constituting the layer structure of the second recognizer is greater than the number of layers constituting the layer structure of the first recognizer, in the second recognizer, the operation load of the image recognition process is greater than that of the first recognizer so that the image recognition process becomes slow, but the recognition accuracy of the image is higher than that of the first recognizer, and thereby it is possible to improve the confidence level for the recognition result.

In the medical image processing device according still another aspect of the invention, the first recognizer and the second recognizer may have at least one filter in the layer constituting the layer structure.

In the medical image processing device according still another aspect of the invention, the number of layers, which constitute the layer structure and have filters, of the second recognizer may be greater than the number of layers, which constitute the layer structure and have filters, of the first recognizer.

In the medical image processing device according still another aspect of the invention, each of the first recognizer and the second recognizer may be a convolutional neural network.

The first recognizer and the second recognizer which are convolutional neural networks have different number of layers including filters. Since the first recognizer has a smaller number of layers including filters, the processing time for the convolutional operation becomes short (operation load becomes low), speeding up of the image recognition process can be possible, and the first recognizer is effective in case of checking the recognition result of the image in real time. Meanwhile, since the second recognizer has a greater number of layers including filters, the processing time for the convolutional operation becomes long (operation load becomes great), the image recognition process becomes slow, but the confidence level for the recognition result of the image is high. Thus, in a case where the confidence level becomes low in the first recognizer, it is possible to correct the recognition by performing recognition again using the second recognizer having higher recognition accuracy than the first recognizer.

In the medical image processing device according still another aspect of the invention, each of the first recognizer and the second recognizer may detect a position of a lesion candidate from the medical image. In this manner, it is possible to cause the display unit to display which region of the medical image the lesion candidate is in.

In the medical image processing device according still another aspect of the invention, each of the first recognizer and the second recognizer may classify the medical image into any category of a plurality of categories relating to a lesion.

In the medical image processing device according still another aspect of the invention, each of the first recognizer and the second recognizer may classify a plurality of lesion regions on the medical image into any category of a plurality of categories relating to a lesion. As the plurality of categories relating to the lesion, for example, there are categories such as "neoplastic", "non-neoplastic", and "others".

In the medical image processing device according still another aspect of the invention, the plurality of categories may be a plurality of categories relating to a type of a lesion, a plurality of categories relating to a disease stage of a lesion, or a plurality of categories in which a type and a disease stage of a lesion are combined. For example, the plurality of categories relating to the disease stage of the lesion are stages I, II, III, IV, and the like indicating the progress degree of the lesion or the like.

In the medical image processing device according still another aspect of the invention, the control unit may cause a display unit to display a recognition result of the medical image by at least one of the first recognizer or the second recognizer. In a case where the confidence level for the recognition result by the first recognizer is high, since the recognition process by the second recognizer is not executed, the recognition result by the first recognizer is displayed on the display unit. Meanwhile, in a case where the confidence level for the recognition result by the first recognizer is low, since the recognition process by the second recognizer is executed, only the recognition result by the second recognizer may be displayed on the display unit or the recognition results of the first recognizer and the second recognizer may be displayed on the display.

In the medical image processing device according still another aspect of the invention, in a case where the second recognizer is used for recognition of the medical image, the control unit may cause the display unit to display information indicating that the second recognizer is used. For example, in a case where the display of the recognition result is delayed, it is possible for the user to grasp that a recognizer (second recognizer having high operation load and long processing time) that is different from a normal recognizer (first recognizer) is used so that the display of the recognition result is delayed and it is possible for the user to check that the confidence level for the recognition result of the lesion is low in the normal recognizer.

In the medical image processing device according still another aspect of the invention, in a case where the second recognizer is used for recognition of the medical image, the control unit may cause the display unit to display information indicating that the recognition process by the second recognizer is in progress for a period from the start to the end of the recognition process by the second recognizer. In a case where the recognition process by the second recognizer is performed, the second recognizer requires more processing time than the first recognizer, and waiting time until the recognition result is displayed becomes long. However, it is possible for the user to check that at least the recognition process is being performed, by displaying the information indicating that the recognition process by the second recognizer is in progress for the waiting time.

The medical image processing device according still another aspect of the invention may further comprise a recording unit that records a recognition result of the medical image by at least one of the first recognizer or the second recognizer.

The medical image processing device according still another aspect of the invention may further comprise a classification selection unit that manually selects a category of the medical image, in which the recognition confidence level determination device determines a confidence level for a category classification of the medical image by the second recognizer, and the control unit causes the display unit to display a category selection menu used for selection of the category of the medical image in a case where the confidence level for the category classification of the medical image is low, and receives selection of the category of the medical image by the classification selection unit using the category selection menu.

In a case where the recognition process by the second recognizer is performed, the confidence level for the recognition result (category classification) of the second recognizer may be lowered in some cases. In this case, in a case where the category classification with a low confidence level is presented to the user, there is a high risk of presenting an incorrect category classification. Thus, the category selection menu is displayed on the display unit so that the selection of the category classification by the user is received.

In the medical image processing device according still another aspect of the invention, the control unit may decide a category priority of the plurality of categories on the basis of a category recognition result of the medical image by the second recognizer, and change a display order of the plurality of categories in the category selection menu according to the category priority. In this manner, it is possible to display the category classification having high possibility to be selected at the top, and it makes it easy for the user to select the category classification.

In the medical image processing device according still another aspect of the invention, in a case where the category of the medical image is decided by the classification selection unit, the control unit may cause the display unit to display information indicating that the category of the medical image is decided by the classification selection unit. In this manner, it is possible to check whether the category classification of the medical image is performed automatically by the medical image processing device, or is selected by the user.

A medical image processing method according to still another aspect of the invention comprises a step of acquiring a medical image including an image of a subject; a step of performing recognition of the medical image using a first recognizer; a step of determining a confidence level for a recognition result by the first recognizer; and a step of performing recognition of the medical image using a second recognizer according to a determination result of the confidence level, the second recognizer having higher recognition accuracy than the first recognizer.

In the medical image processing method according still another aspect of the invention, in a case where the confidence level for the recognition result of the medical image by the first recognizer is equal to or greater than a reference value, the recognition result by the first recognizer may be displayed on a display unit, and in a case where the confidence level for the recognition result of the medical image by the first recognizer is less than the reference value, the recognition result by the second recognizer may be displayed on the display unit.

A medical image processing program according to still another aspect of the invention causes a computer to execute a function of acquiring a medical image including an image of a subject; a function of performing recognition of the medical image using a first recognizer; a function of determining a confidence level for a recognition result by the first recognizer; and a function of performing recognition of the medical image using a second recognizer according to a determination result of the confidence level, the second recognizer having higher recognition accuracy than the first recognizer.

In the medical image processing program according still another aspect of the invention, in a case where the confidence level for the recognition result of the medical image by the first recognizer is equal to or greater than a reference value, the recognition result by the first recognizer may be displayed on a display unit, and in a case where the confidence level for the recognition result of the medical image by the first recognizer is less than the reference value, the recognition result by the second recognizer may be displayed on the display unit.

According to the invention, by using a first recognizer that performs recognition of a medical image and a second recognizer that has higher recognition accuracy than the first recognizer, it is possible to speed up an image recognition process by the first recognizer and improve the recognition accuracy by the second recognizer.

BRIEF DESCRIPTION OF THE DRAWINGS

FIG. 7 is a flowchart showing an embodiment of a medical image processing method.

DESCRIPTION OF THE PREFERRED EMBODIMENTS

Hereinafter, preferred embodiments of a medical image processing device, a medical image processing method, and a medical image processing program according to the invention will be described with reference to accompanying drawings.

[Entire Configuration of Endoscope System]

Figure 1:
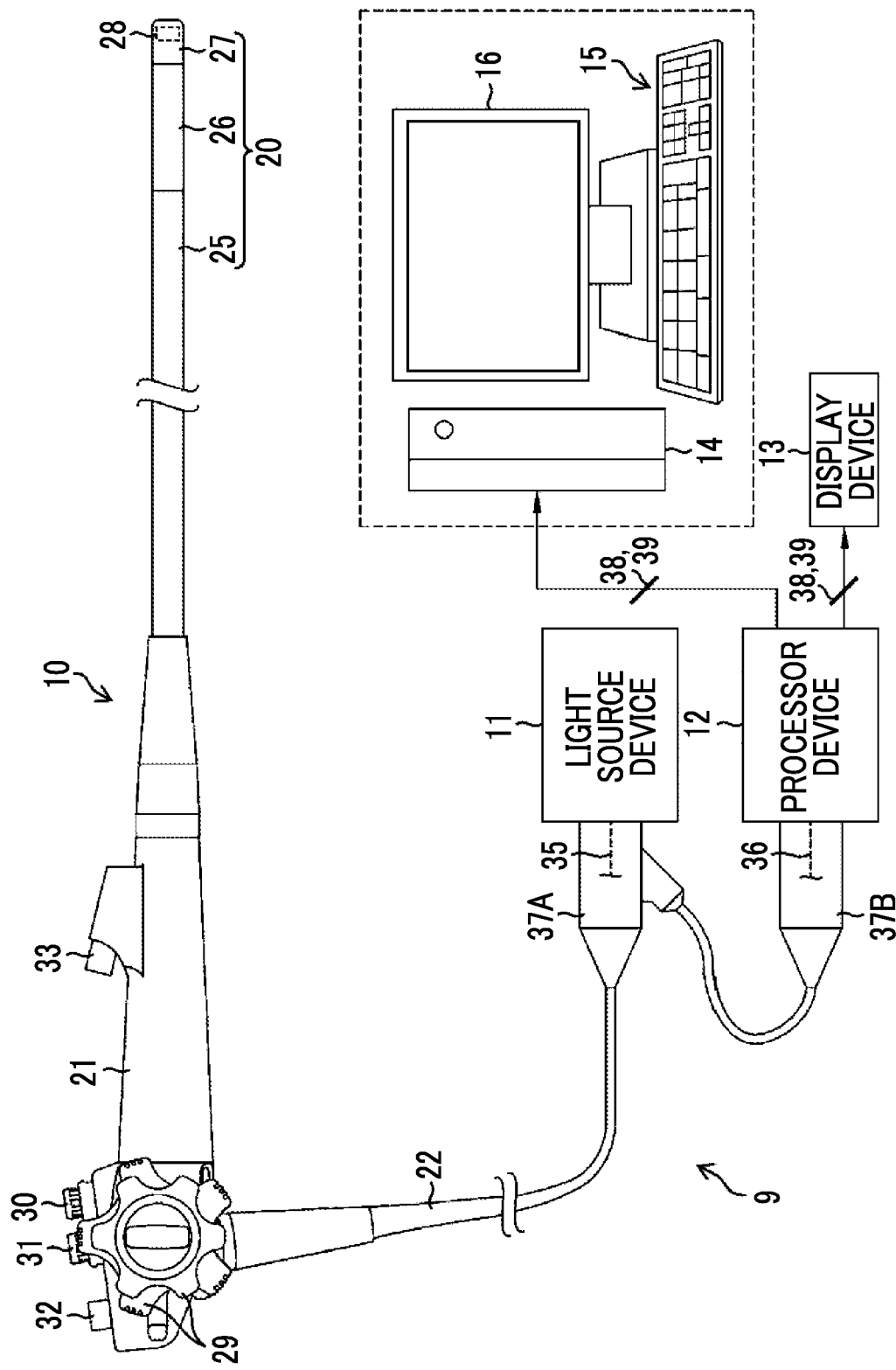
FIG. 1 is a schematic diagram showing the entire configuration of an endoscope system.

FIG. 1 is a schematic diagram showing the entire configuration of an endoscope system 9 including a medical image processing device according to an embodiment of the invention. As shown in FIG. 1, the endoscope system 9 includes an endoscope 10 which is an electronic endoscope, a light source device 11, a processor device 12, a display device 13, a medical image processing device 14, an operation unit 15, and a display unit 16.

The endoscope 10 corresponds to a medical device of an embodiment of the invention, and is a flexible endoscope, for example. The endoscope 10 includes an insertion part 20 that is to be inserted into an object to be examined and has a distal end and a proximal end, a hand operation part 21 that is provided to be continuous to the proximal end side of the insertion part 20 and is held by an operator to perform various operations, and a universal cord 22 that is provided to be continuous to the hand operation part 21.

The insertion part 20 is formed in a long shape with a small diameter as a whole. The insertion part 20 is configured by a soft portion 25 having flexibility, a bendable portion 26 that is bendable by an operation of the hand operation part 21, and a distal end portion 27 in which an imaging optical system (not shown), an image pick-up element 28, and the like are built, which are continuously provided in order from the proximal end side to the distal end side.

The image pick-up element 28 is a complementary metal oxide semiconductor (CMOS) type or charge coupled device (CCD) image pick-up element. Image light of an observation site is incident on an image pick-up surface of the image pick-up element 28 via an observation window (not shown) open in the distal end surface of the distal end portion 27 and the imaging optical system (not shown) disposed behind the observation window. The image pick-up element 28 performs image pick-up (conversion into electrical signals) of the image light of the observation site, which is incident on the image pick-up surface, and outputs an image pick-up signal.

Various operation members to be operated by an operator are provided in the hand operation part 21. Specifically, the hand operation part 21 is provided with two kinds of bendable operation knobs 29 used for the bendable operation of the bendable portion 26, an air/water supply button 30 for an air/water supply operation, and a suction button 31 for a suction operation. The hand operation part 21 is provided with a static image capturing instruction portion 32 for performing an imaging instruction of a static image 39 of the observation site, and a treatment tool inlet 33 through which a treatment tool (not shown) is inserted into a treatment tool passage (not shown) inserted into the insertion part 20.

The universal cord 22 is a connection cord for connecting the endoscope 10 to the light source device 11. The universal cord 22 includes a light guide 35, a signal cable 36, and a fluid tube (not shown) which are inserted into the insertion part 20. In addition, the end portion of the universal cord 22 is provided with a connector 37A connected to the light source device 11, and a connector 37B which branches from the connector 37A and is connected to the processor device 12.

The connector 37A is connected to the light source device 11 so that the light guide 35 and the fluid tube (not shown) are inserted into the light source device 11. In this manner, required illumination light, water, and air are supplied from the light source device 11 to the endoscope 10 via the light guide 35 and the fluid tube (not shown). As a result, illumination light is emitted to the observation site from the illumination window (not shown) of the distal end surface of the distal end portion 27. According to a pressing operation of the air/water supply button 30, air or water is sprayed from an air/water supply nozzle (not shown) of the distal end surface of the distal end portion 27 toward the observation window (not shown) of the distal end surface.

The connector 37B is connected to the processor device 12 so that the signal cable 36 and the processor device 12 are electrically connected to each other. In this manner, an image pick-up signal of the observation site is output from the image pick-up element 28 of the endoscope 10 to the processor device 12 via the signal cable 36, and a control signal is output from the processor device 12 to the endoscope 10 via the signal cable 36.

In the embodiment, a flexible endoscope is described as an example of the endoscope 10, but various endoscopes which can capture a video of the observation site, such as a rigid endoscope may be used.

The light source device 11 supplies illumination light to the light guide 35 of the endoscope 10 via the connector 37A. As the illumination light, light in various wavelength ranges is selected according to the observation purpose, such as white light (light in white-light wavelength range or light in a plurality of wavelength ranges) or light in one or a plurality of specific wavelength ranges, or a combination thereof. The specific wavelength range is a range narrower than the white-light wavelength range.

A first example of the specific wavelength range is a blue-light wavelength range or a green-light wavelength range of a visible-light wavelength range, for example. The wavelength range of the first example includes a wavelength range of 390 nm to 450 nm or 530 nm to 550 nm, and light of the first example has a peak wavelength in a wavelength range of 390 nm to 450 nm or 530 nm to 550 nm.

A second example of the specific wavelength range is a red-light wavelength range of a visible-light wavelength range, for example. The wavelength range of the second example includes a wavelength range of 585 nm to 615 nm or 610 nm to 730 nm, and light of the second example has a peak wavelength in a wavelength range of 585 nm to 615 nm or 610 nm to 730 nm.

A third example of the specific wavelength range includes a wavelength range where a light absorption coefficient in oxyhemoglobin is different from that in reduced hemoglobin, and light of the third example has a peak wavelength in a wavelength range where a light absorption coefficient in oxyhemoglobin is different from that in reduced hemoglobin. The wavelength range of the third example includes a wavelength range of 400±10 nm, 440±10 nm, 470±10 nm, or 600 nm to 750 nm, and light of the third example has a peak wavelength in a wavelength range of 400±10 nm, 440±10 nm, 470±10 nm, or 600 nm to 750 nm.

A fourth example of the specific wavelength range is a wavelength range (390 nm to 470 nm) of excitation light which is used for observation (fluorescence observation) of fluorescence emitted by fluorescent materials in a living body and excites the fluorescent materials.

A fifth example of the specific wavelength range is an infrared wavelength range. The wavelength range of the fifth example includes a wavelength range of 790 nm to 820 nm or 905 nm to 970 nm, and light of the fifth example has a peak wavelength in a wavelength range of 790 nm to 820 nm or 905 nm to 970 nm.

The processor device 12 controls the operation of the endoscope 10 via the connector 37B and the signal cable 36. In addition, the processor device 12 generates a video 38 of the observation site on the basis of an image pick-up signal acquired from the image pick-up element 28 of the endoscope 10 via the connector 37B and the signal cable 36. Further, in a case where the static image capturing instruction portion 32 is operated in the hand operation part 21 of the endoscope 10, the processor device 12 generates a static image 39 of the observation site on the basis of the image pick-up signal acquired from the image pick-up element 28 in parallel with the generation of the video 38. The static image 39 may be generated to have higher resolution than the video 38.

The video 38 and the static image 39 are in-vivo images captured in the object to be examined, that is, in the living body. Further, in a case where the video 38 and the static image 39 are images obtained by light (special light) in the above-described specific wavelength range, the video 38 and the static image 39 are special light images. The processor device 12 outputs the generated video 38 and static image 39 to each of the display device 13 and the medical image processing device 14.

The processor device 12 may generate (acquire) a special light image having information of the above-described specific wavelength range on the basis of a normal light image obtained by the above-described white light. In this case, the processor device 12 functions as a special light image acquisition unit. The processor device 12 acquires a signal of the specific wavelength range by performing an arithmetic operation based on color information about red, green, blue (RGB) or cyan, magenta, and yellow (CMY) included in the normal light image.

The processor device 12 may generate a feature quantity image such as a known oxygen saturation image on the basis of at least one of the normal light image obtained by the above-described white light or the special light image obtained by the light (special light) in the above-described specific wavelength range. In this case, the processor device 12 functions as a feature-quantity-image generation unit. The video 38 or the static image 39 including the in-vivo image, the normal image, the special light image, and the feature quantity image is a medical image which is obtained by imaging a human body or is obtained by visualizing the measured result for the purpose of diagnosis and inspection by the image.

The display device 13 is connected to the processor device 12 and displays the video 38 and the static image 39 input from the processor device 12. The user (doctor) performs an advance/retraction operation of the insertion part 20 while checking the video 38 displayed on the display device 13, and in a case where a lesion or the like is found in the observation site, the user (doctor) operates the static image capturing instruction portion 32 to execute static image capturing of the observation site and performs diagnosis, biopsies, and the like.

[Medical Image Processing Device]

As the medical image processing device 14, for example, a personal computer is used in the embodiment. A keyboard, a mouse, or the like connected to the personal computer in a wired or wireless manner is used as the operation unit 15, and various monitors such as a liquid crystal monitor that can be connected to the personal computer are used as the display unit 16.

In addition, a diagnosis support apparatus such as a work station (server) may be used as the medical image processing device 14, and in this case, the operation unit 15 and the display unit 16 are provided to each of a plurality of terminals connected to the work station. Further, as the medical image processing device 14, a medical service support device that supports the creation of a medical report or the like may be used, for example.

The medical image processing device 14 is a portion that mainly performs recognition of the video 38 or the static image 39 (medical image) and a category classification of the medical image, and performs acquisition and storage of the medical image, reproduction control of the medical image, and display of the recognition result (category classification). The operation unit 15 is used for inputting an operation instruction to the medical image processing device 14. The display unit 16 displays the video 38 or the static image 39, displays the recognition result such as the category classification of the medical image, and displays a category selection menu which will be described below, under the control of the medical image processing device 14. Further, the display unit 16 cooperates with the operation unit 15 to serve as a part of a user interface functioning as a classification selection unit that manually selects a category of the medical image.

<Function of Medical Image Processing Device>

Figure 2:
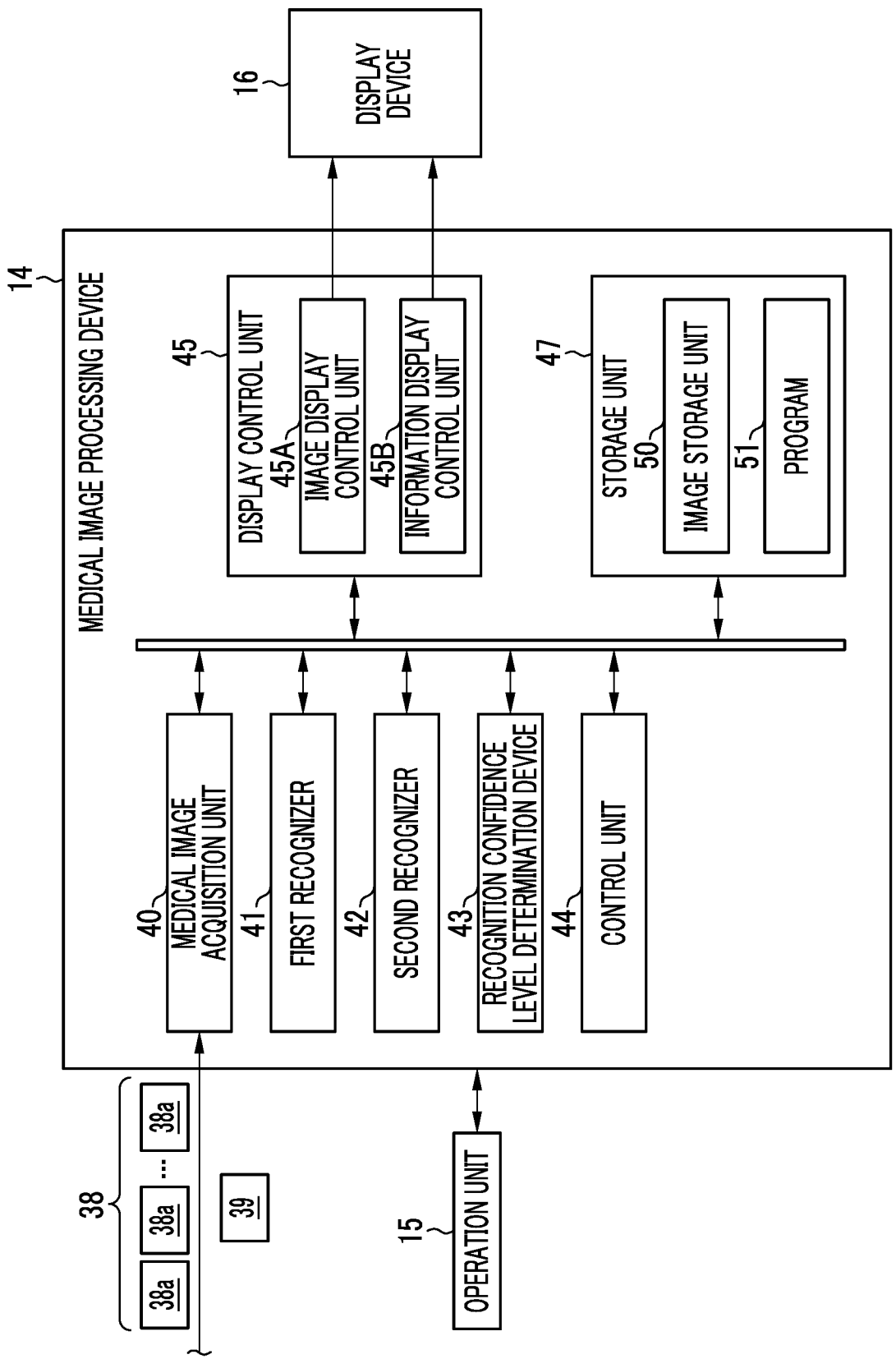
FIG. 2 is a functional block diagram showing functions of a medical image processing device.

FIG. 2 is a functional block diagram showing functions of the medical image processing device 14. As shown in FIG. 2, a hardware structure which executes various controls of the medical image processing device 14 including display of the video 38 or the static image 39, recognition of the medical image, display of the recognition result, and the like is various processors described below. The various processors include a central processing unit (CPU) as a general-purpose processor executing software (program) and functioning as various control units, a programmable logic device (PLD) as a processor of which the circuit configuration can be changed after manufacturing such as a field programmable gate array (FPGA), a dedicated electrical circuit as a processor having a circuit configuration designed exclusively for executing a specific process such as an application specific integrated circuit (ASIC).

One processing unit may be configured by one processor among these various processors, or may be configured by two or more same or different kinds of processors (for example, a combination of a plurality of FPGAs or a combination of the CPU and the FPGA). Further, a plurality of control units may be configured by one processor. As an example where a plurality of control units are configured by one processor, first, there is an aspect where one processor is configured by a combination of one or more CPUs and software as typified by a computer, such as a client or a server, and this processor functions as a plurality of control units. Second, there is an aspect where a processor fulfilling the functions of the entire system including a plurality of control units by one integrated circuit (IC) chip as typified by a system on chip (SoC) or the like is used. In this way, various control units are configured using one or more of the above-described various processors as hardware structures.

A control unit 44 corresponding to the processor (not shown) of the medical image processing device 14 generally controls a medical image acquisition unit 40, a first recognizer 41, a second recognizer 42, a recognition confidence level determination device 43, and a display control unit 45 on the basis of a program (medical image processing program) 51 stored in a storage unit 47, and functions as a part of these units.

The storage unit 47 functions as a recording unit that records a recognition result by at least one of the first recognizer 41 or the second recognizer 42 and an image storage unit 50 that stores the captured video 38 and static image 39, and the program 51 and information according to various controls of the medical image processing device 14 are stored in the storage unit 47.

In the embodiment, the storage unit 47 is provided in the medical image processing device 14, but the storage unit 47 may be provided in a server or a database on the Internet. Therefore, the medical image processing device of the embodiment of the invention also includes a medical image processing system configured by a plurality of devices.

The medical image acquisition unit 40 acquires the medical image (in this example, video 38 captured by the endoscope 10) including a subject image from the processor device 12 using an image input/output interface (not shown) connected to the processor device 12 (FIG. 1) in a wired or wireless manner. In addition, in a case where the static image 39 is captured while the video 38 is being captured in the endoscope 10, the medical image acquisition unit 40 acquires the video 38 and the static image 39 from the processor device 12. Then, the medical image acquisition unit 40 stores the acquired video 38 and static image 39 in the image storage unit 50 in the storage unit 47. The reference signs 38a in the drawing indicate a plurality of frame images constituting the video 38.

The medical image acquisition unit 40 may acquire the video 38 and the static image 39 via various information storage mediums such as a memory card instead of directly acquiring the video 38 and the static image 39 from the processor device 12. Further, the medical image acquisition unit 40 may acquire, via the Internet, the video 38 and the static image 39 uploaded to a server or a database on the Internet.

In a case where the medical image acquisition unit 40 acquires the special light image having information of the specific wavelength range, as the video 38 and the static image 39, the medical image acquisition unit 40 functions as the special light image acquisition unit.

Further, in a case where static image capturing of the observation site is performed according to the operation of the static image capturing instruction portion 32, the medical image acquisition unit 40 may cause the image storage unit 50 to store the video 38 for one minute before and after the static image capturing (for one minute before the static image capturing to one minute after the static image capturing) without causing the image storage unit 50 to necessarily store the full video 38 input from the processor device 12 or the like.

The first recognizer 41 is a portion that performs recognition of the image (video 38 and static image 39) captured during the observation of the body cavity, and in this example, the first recognizer 41 includes a convolutional neural network (CNN) which calculates a feature quantity from an image by learning to perform an image recognition process, and calculates a feature quantity using color information, a pixel value gradient, and the like in the image. The first recognizer 41 detects a lesion (lesion candidate) on the image using the calculated feature quantity, and obtains a first recognition result of a category classification indicating which of a plurality of categories relating to a lesion, such as "neoplastic", "non-neoplastic", and "others" the medical image belongs to.

Figure 3:
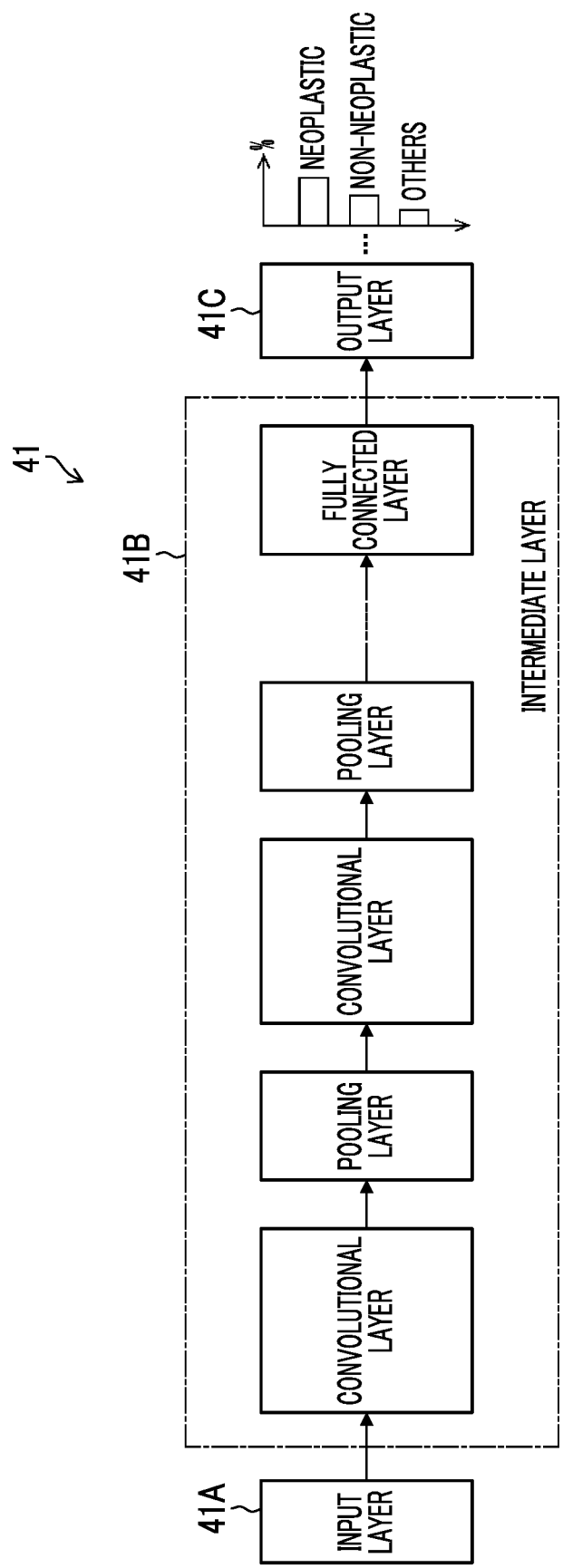
FIG. 3 is a schematic diagram showing a typical configuration example of a CNN applied to a first recognizer.

FIG. 3 is a schematic diagram showing a typical configuration example of the CNN applied to the first recognizer 41.

As shown in FIG. 3, the CNN includes an input layer 41A, an intermediate layer 41B, and an output layer 41C, and the layers have a structure in which a plurality of "nodes" are connected by "edges". The intermediate layer 41B includes a plurality of sets of a convolutional layer and a pooling layer, and a fully connected layer.

An image to be subjected to the recognition process is input to the input layer 41A.

The intermediate layer 41B includes a plurality of sets of a convolutional layer and a pooling layer, and a fully connected layer, and extracts features from the image input from the input layer. The convolutional layer performs a filter process on the node near the previous layer (performs convolutional operation using a filter), and acquires "feature maps". The pooling layer reduces the feature map output from the convolutional layer, and sets the reduced feature map as a new feature map. The "convolutional layer" plays a role of extracting features from the image, such as edge extraction, and the "pooling layer" plays a role of giving robustness so that the extracted features are not affected by translation or the like.

The intermediate layer 41B is not limited to a case in which the convolutional layer and the pooling layer are set as one set, and includes a case in which the convolutional layers are continuous, and a normalization layer. Parameters of the filters used in each convolutional layer are automatically learned in advance by an amount of learning data.

The output layer 41C outputs the recognition result for each classification of the image on the basis of the features extracted by the intermediate layer 41B. In this example, the image is classified into three categories of "neoplastic", "non-neoplastic", and "others", and the recognition result is output as three scores corresponding to "neoplastic", "non-neoplastic", and "others" (the sum of the three scores is 100%).

Returning to FIG. 2, the second recognizer 42 has the same configuration as the first recognizer 41, and performs a recognition process of the captured image to obtain a second recognition result of a category classification or the like. However, the second recognizer 42 is different from the first recognizer 41 in that the recognition accuracy of the image is higher than that of the first recognizer 41, the operation load of the recognition process is greater than that of the first recognizer 41, and the time for the image recognition process becomes longer.

Specifically, in the second recognizer 42, the number of layers of the CNN having the layer structure is greater than that of the first recognizer 41, and particularly, the number of convolutional layers having filters in the intermediate layer is greater than that of the first recognizer 41. The second recognizer 42 uses a part of the first recognizer 41 in common, and for example, a certain "feature map" of the intermediate layer 41B of the first recognizer 41 is input to the second recognizer 42. In this case, the number of convolutional layers in the intermediate layer of the second recognizer 42 is greater than the number of convolutional layers which are after the certain "feature map", in the intermediate layer of the first recognizer 41.

The recognition confidence level determination device 43 is a portion that determines the confidence level for the recognition result by the first recognizer 41, and the recognition confidence level determination device 43 calculates the confidence level from the recognition result (for example, scores of likeness to lesions) of the first recognizer 41, and in this example, determines whether the confidence level is "high" or "low". The scores of likeness to lesions may be used as the confidence level.

Specifically, the recognition confidence level determination device 43 inputs the recognition result (in this example, three scores) of the first recognizer 41, and in a case where the difference between the highest score among the three scores and the other scores is large, the recognition confidence level determination device 43 classifies the image into a category having the highest score, and determines that the confidence level for the category classification is "high". Conversely, in a case where the difference between the scores of the categories is small, the recognition confidence level determination device 43 classifies the image into a category having the highest score, and determines that the confidence level for the category classification is "low".

For example, in a case where the score (confidence level) of "neoplastic" is 80%, the score of "non-neoplastic" is 15%, and the score of "others" is 5%, since the score of "neoplastic" is prominent, the confidence level for the category classification that the image to be recognized is classified to "neoplastic" is determined to be "high". In a case where the score of "neoplastic" is 33%, the score of "non-neoplastic" is 30%, and the score of "others" is 37%, among these scores, since the difference between the highest score (37%) of "others" and the scores (30% and 33%) of the other categories (particularly the second highest score 33%) is small, the confidence level for the category classification that the image to be recognized is classified to "others" is determined to be "low".

The result of determining whether the confidence level is "high" or "low" can be decided by whether the difference between the highest score and the second highest score is equal to or greater than a first reference value, or can be determined by whether a ratio between the highest score and the second highest score is equal to or greater than a second reference value. Further, the first reference value or the second reference value (hereinafter, simply referred to as the "reference value") may be a preset fixed value or a value set by a user.

The recognition confidence level determination device 43 can perform the determination on the confidence level for the recognition result by the second recognizer 42 similar to the determination on the confidence level for the recognition result by the first recognizer 41. In this case, since the second recognizer 42 has higher recognition accuracy of the image than the first recognizer 41, the reference value used at the time of determining the confidence level for the recognition result obtained by the second recognizer 42 may be smaller than the reference value used at the time of determining the confidence level for the recognition result obtained by the first recognizer 41.

The control unit 44 causes the second recognizer 42 to execute the recognition process of the medical image according to the determination result of the recognition confidence level determination device 43. That is, in a case where the recognition confidence level determination device 43 determines that the confidence level for the recognition result by the first recognizer 41 is "low", the control unit 44 causes the second recognizer 42 to perform the recognition process of the medical image of which the confidence level is determined to be "low".

That is, the control unit 44 causes the first recognizer 41 to perform the image recognition process in advance, and in a case where the recognition confidence level determination device 43 determines that the confidence level for the recognition result of the image by the first recognizer 41 is "low", the control unit 44 causes the second recognizer 42 to perform the image recognition process.

In a case where it is determined that the confidence level for the recognition result of the image by the second recognizer 42 is "low", the control unit 44 causes the display unit 16 to display a category selection menu or the like which is used for the category selection by the user, and receives the category selection of the medical image by using the category selection menu. The category classification of the medical image performed by the user will be described below in detail.

It is preferable that the control unit 44 causes a recording unit (storage unit 47 or header section of an image file) to record a recognition result of the medical image by at least one of the first recognizer 41 or the second recognizer 42, in association with the corresponding medical image.

The display control unit 45 controls the display by the display unit 16. The display control unit 45 functions as an image display control unit 45A and an information display control unit 45B.

The image display control unit 45A causes the display unit 16 to display the video 38 and the static image 39 which are being captured, or performs control of causing the display unit 16 to reproduce the video 38 (static image 39 is also possible) stored in each folder in the image storage unit 50.

The information display control unit 45B functions as a control unit that causes the display unit 16 to display required information other than images, such as at least one of the first recognition result by the first recognizer 41 or the second recognition result by the second recognizer 42.

Figure 4:
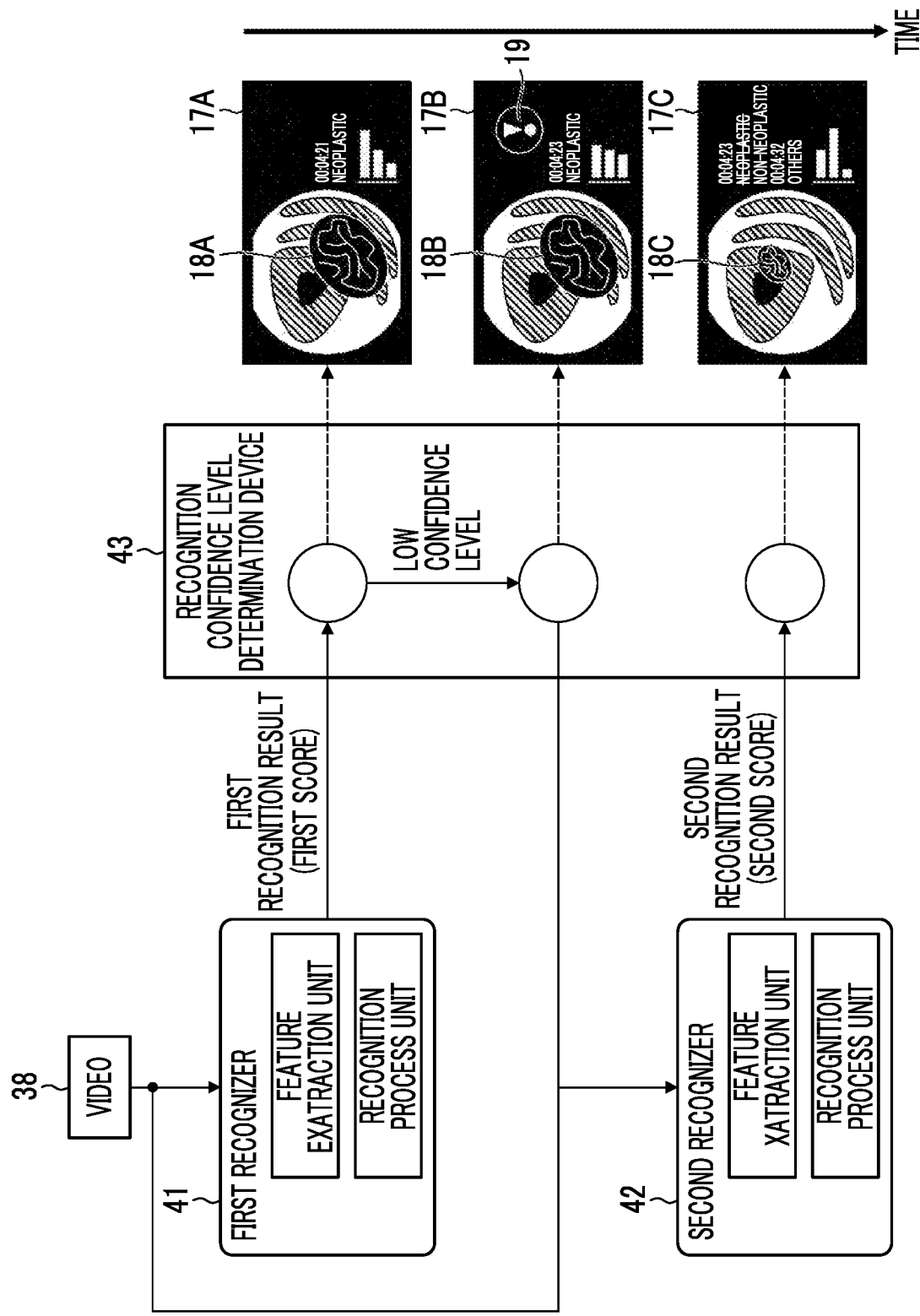
FIG. 4 is a diagram for describing operations of the first recognizer, a second recognizer, a recognition confidence level determination device, and an information display control unit on a video.

FIG. 4 is a diagram for describing operations of the first recognizer 41, the second recognizer 42, the recognition confidence level determination device 43, and the information display control unit 45B on the video 38.

In FIG. 4, the video 38 captured by the endoscope system 9 is input to the first recognizer 41 and the second recognizer 42 via the medical image acquisition unit 40.

The first recognizer 41 includes a feature extraction unit and a recognition process unit, performs image recognition for each of frame images 38a (or frame images 38a at regular intervals) constituting the input video 38, and outputs the first recognition result (three first scores indicating "neoplastic", "non-neoplastic", and "others") to the recognition confidence level determination device 43.

The recognition confidence level determination device 43 determines the confidence level for the category classification specified by the highest score among the three first scores on the basis of the three first scores which are input.

In FIG. 4, screens 17A, 17B, and 17C indicate screens at different time of the display unit 16, and images captured at time "00:04:21", "00:04:23", and "00:04:32" each indicating an elapsed time from a start time point of capturing the video 38, and the like are displayed on the screens 17A, 17B, and 17C.

In the example shown in FIG. 4, the recognition confidence level determination device 43 determines that the confidence level for the category classification, which is specified by the highest first score, of each of the frame images 38a captured at time "00:04:21" and "00:04:32" is "high", and determines that the confidence level for the category classification, which is specified by the highest first score, of the image captured at time "00:04:23" is "low".

The information display control unit 45B displays various information (in this example, imaging time, category classification, and recognition result) in a region on the right side of each of the screens 17A, 17B, and 17C. The category classifications of the images captured at time "00:04:21", "00:04:23", and "00:04:32" based on the first recognition result are respectively "neoplastic", "neoplastic", and "others", and thus "neoplastic", "neoplastic", and "others" are respectively displayed on the screens 17A, 17B, and 17C. Further, the recognition results expressed by bar graphs are displayed below the category classification by the information display control unit 45B.

Each of the first recognizer 41 and the second recognizer 42 has a function of detecting the position of the lesion candidate from the medical image, and the information display control unit 45B can cause indexes 18A, 18B, and 18C indicating the lesion candidates to be displayed on the image in an overlapping manner, on the basis of the positions of the lesion candidates detected by the first recognizer 41 and the second recognizer 42.

The second recognizer 42 includes a feature extraction unit and a recognition process unit, performs image recognition of the frame image 38a which constitutes the input video 38 and is according to the determination result of the confidence level (determination result in which the confidence level is "low") which is obtained by the recognition confidence level determination device 43 on the basis of the first recognition result by the first recognizer 41, and outputs the second recognition result.

In the example shown in FIG. 4, since the recognition confidence level determination device 43 determines that the confidence level for the category classification, which is specified by the highest first score, of the frame image 38a captured at time "00:04:23" is "low", the second recognizer 42 performs the recognition process of the frame image 38a captured at time "00:04:23" and outputs the second recognition result.

In this example, for the frame image 38a captured at time "00:04:23", the first recognition result by the first recognizer 41 and the second recognition result by the second recognizer 42 are different, the category classification of the image is "neoplastic" in the first recognition result, and the category classification of the image is changed (modified) to "non-neoplastic" in the second recognition result.

Further, the modified contents of the category classification by the second recognizer 42 are displayed on the screen 17C in which the image captured at time "00:04:32" is displayed. That is, the control unit 44 or the information display control unit 45B displays time "00:04:23" and "neoplastic" with strikethrough, and modified "non-neoplastic" on a region above time "00:04:32" on the screen 17C of the display unit 16.

With this display aspect, it is possible for the user to know that the category classification of the frame image 38a captured at time "00:04:23" is changed from "neoplastic" to "non-neoplastic". Further, it is possible for the user to know that the second recognizer 42 is used for the frame image 38a captured at time "00:04:23". That is, in a case where the second recognizer 42 is used for recognition of the medical image, the control unit 44 or the information display control unit 45B indirectly displays information indicating that the second recognizer 42 is used by displaying two recognition results (first and second recognition results and the modified contents of the first recognition result).

Further, it is determined that the confidence level for the first recognition result of the frame image 38a captured at time "00:04:23" by the first recognizer 41 is "low", and thus the recognition process of the same frame image 38a by the second recognizer 42 is started. In a case where the recognition process by the second recognizer 42 is performed, the second recognizer 42 requires more processing time than the first recognizer 41, and it takes some time until the second recognizer 42 acquires the second recognition result while the first recognizer 41 acquires the first recognition result in substantially real time.

In a case where the second recognizer 42 performs the image recognition process, the control unit 44 or the information display control unit 45B causes the display unit 16 to display information indicating that the recognition process by the second recognizer 42 is in progress for a period from the start to the end of the recognition process.

In the example shown in FIG. 4, in the screen 17B of the display unit 16, information 19 indicating that the recognition process by the second recognizer 42 is in progress is displayed. It is possible for the user to check that at least the recognition process is being performed, by the information 19, and it is possible for the user to check that the confidence level for the current recognition result is "low".

With the medical image processing device 14, even in a case where the acquisition or display of the recognition result is required in real time such as in a case where the video is the recognition target, the first recognizer 41 capable of operating at high speed can acquire the first recognition result in substantially real time (speeding up of the image recognition process), and in a case where the recognition result with a high confidence level cannot be obtained by the first recognizer 41, since the second recognizer 42 with a low speed of the image recognition process and high recognition accuracy is used, it is possible to improve the confidence level for the category classification of the image.

Figure 5:
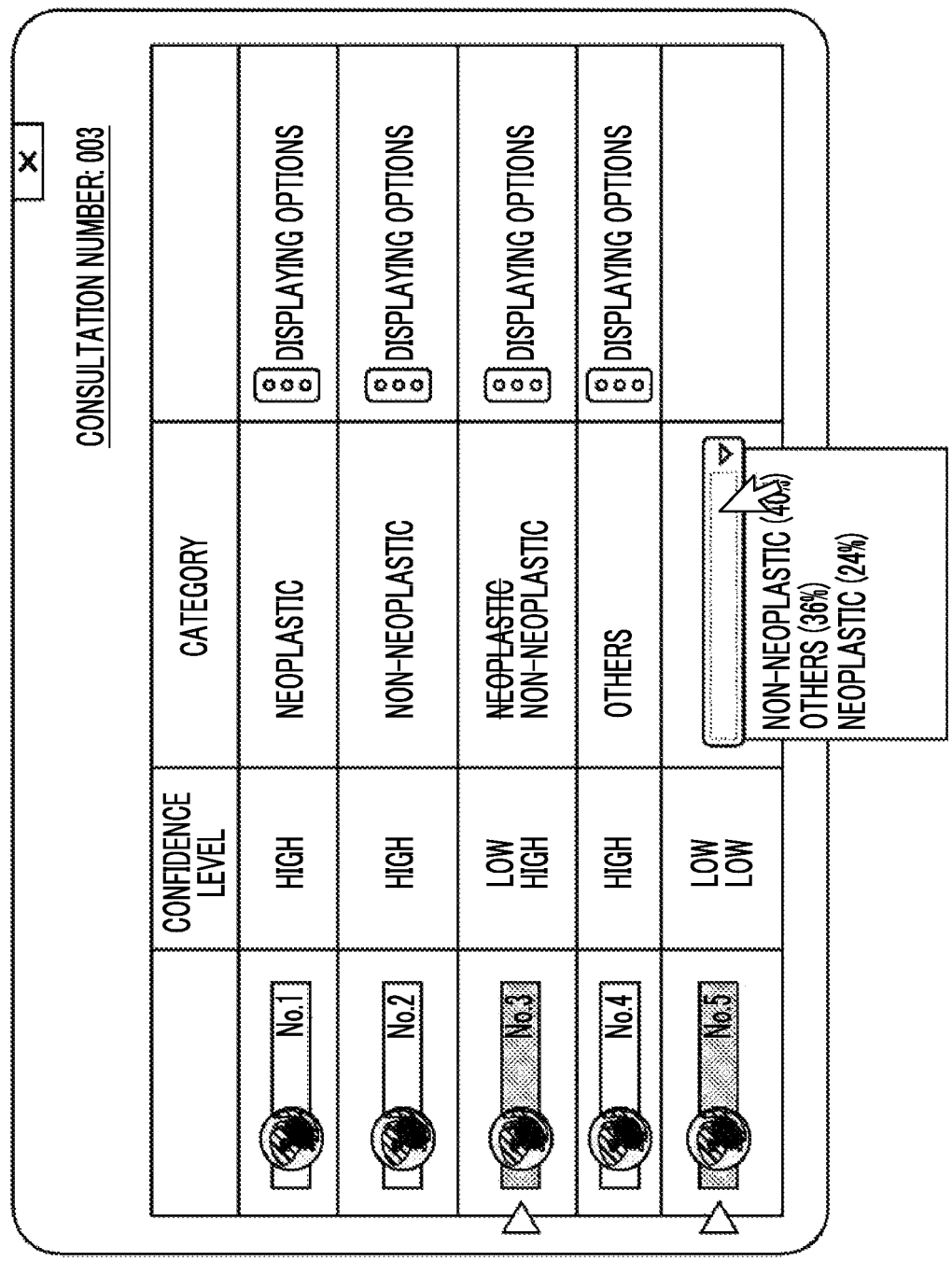
FIG. 5 is a diagram showing an embodiment of information to be displayed on a display unit by the medical image processing device.

FIG. 5 is a diagram showing an embodiment of information to be displayed on the display unit 16 by the medical image processing device 14. The medical image processing device 14 can cause the screen of the display unit 16 to display the category classification of the medical image, the confidence level for the category classification, and the like.

In the screen shown in FIG. 5, the confidence level for the category classification, the category classification, and information "displaying options" for instructing the display of options are displayed in association with identification information (No. 1, No. 2, No. 3, and the like) specifying a plurality of medical images (a plurality of static images captured during the observation by the endoscope) of a patient with a consultation number "003".

In a field indicating the confidence level for the category classification, the determination result ("high" or "low") determined by the recognition confidence level determination device 43 is displayed, and in a field of the category, the category classification ("neoplastic", "non-neoplastic", "others") recognized by the first recognizer 41 and the second recognizer 42 and a "window" for the category selection menu are displayed.

In the example shown in FIG. 5, the confidence levels for the category classifications "neoplastic", "non-neoplastic", and "others" of the images of "No. 1", "No. 2", and "No. 4" are high.

The confidence level for the category classification of the first recognition result "neoplastic" of the image of "No. 3" by the first recognizer 41 is low, and the confidence level for the category classification of the second recognition result "non-neoplastic" of the image of "No. 3" by the second recognizer 42 is high. That is, for the image of "No. 3", the recognition processes by the first recognizer 41 and the second recognizer 42 are performed, and the first recognition result "neoplastic" is changed to the second recognition result "non-neoplastic".

Meanwhile, the confidence level for the category classification based on each of the first and second recognition results of the image of "No. 5" by the first recognizer 41 and the second recognizer 42 is low, and in this case, the field of the category, the "window" for the category selection menu functioning as the classification selection unit that manually selects the category classification is displayed.

The user can cause the category selection menu to be displayed as a pull-down menu by operating the mouse functioning as the operation unit 15 to place the cursor on the "window" and clicking the "window".

In a case where the category selection menu is displayed, it is preferable that the control unit 44 decides a category priority of the plurality of categories on the basis of the category recognition result of the image by the second recognizer 42, changes the display order of the plurality of categories in the category selection menu according to the category priority, and causes the display unit 16 to display the changed display order.

In the category selection menu shown in FIG. 5, among three scores corresponding to "neoplastic", "non-neoplastic", and "others", in the descending order of the scores, "non-neoplastic", "others", and "neoplastic" are displayed.

It is possible for the user to select the category classification of the image of No. 5 from the category selection menu. The category classification selected by the user becomes the category classification of the image of No. 5, and the selected category classification is displayed on the "window".

In a case where in the field of the category, the category classification is displayed using the "window", it is possible for the user to know that the category classification of the corresponding image is decided by the user. That is, the "window" in which the category classification is displayed becomes information indicating that the category classification of the image is decided by the user.

Even in case of the image of which the category classification is automatically decided, it is possible to display the "window" for the category selection menu in the field of the category by clicking an icon button "displaying options", and it is possible for the user to manually change the category classification using the category selection menu.

Further, it is preferable that the image with the low confidence level for the category classification (images of "No. 3" and "No. 5") is displayed in a distinguishable manner with respect to the image with the high confidence level for the category classification (images of "No. 1", "No. 2", and "No. 4"). In the example shown in FIG. 5, "cursors" are displayed at the positions of the images of "No. 3" and "No. 5" with the low confidence level. For the images of "No. 3" and "No. 5" with the low confidence level where the "cursor" is displayed, since the recognition process by the second recognizer 42 is performed, the "cursor" becomes information indicating that the second recognizer 42 is used. The display can be performed in a distinguishable manner using, for example, color coding, instead of displaying the "cursor".

Further, by clicking the identification information (No. 1, No. 2, No. 3, and the like) specifying the image, it is possible to display the image corresponding to the identification information in an enlarged manner by switching the screen of the display unit 16 or display the image in an enlarged manner on a different window.

Figure 6:
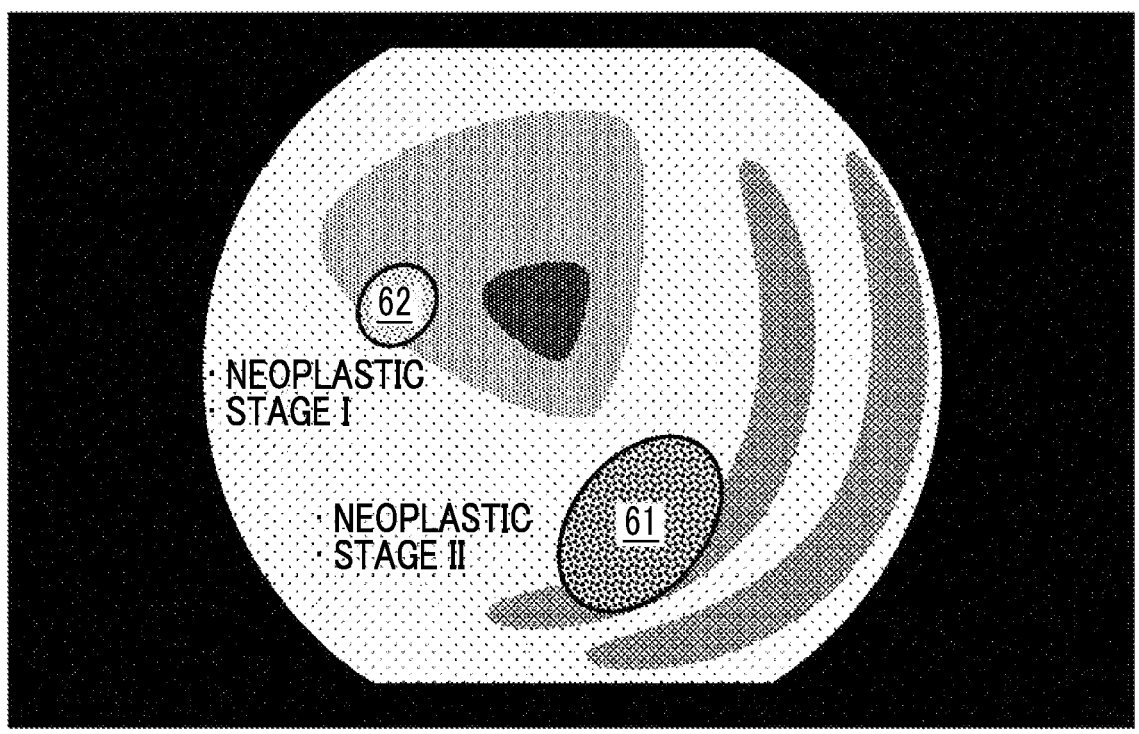
FIG. 6 is a diagram showing another embodiment of an image and information to be displayed on the display unit by the medical image processing device.

FIG. 6 is a diagram showing another embodiment of the image and information to be displayed on the display unit 16 by the medical image processing device 14, and relates to a display aspect in a case where a plurality of lesion regions are detected from one medical image and a case where disease stages are included as the category classification.

In a case where a plurality of lesion regions 61 and 62 are detected as shown in FIG. 6, the first recognizer 41 or the second recognizer 42 performs the recognition process for each of lesion regions 61 and 62 and outputs the recognition result (category classification of lesion for each lesion region).

In the embodiment shown in FIG. 6, the first recognizer 41 or the second recognizer 42 can perform a classification for a plurality of categories (for example, "neoplastic", "non-neoplastic", and "others") relating to the type of lesions, and a classification for a plurality of categories relating to the disease stage of the lesion. The plurality of categories relating to the disease stage of the lesion are stages I, II, III, IV, and the like indicating the progress degree of the lesion or the like.

The control unit 44 or the information display control unit 45B displays the category classifications near the lesion regions 61 and 62 on the screen of the display unit 16 on the basis of the recognition result (category classification of each lesion region) for each of the lesion regions 61 and 62 by the first recognizer 41 or the second recognizer 42.

In the example shown in FIG. 6, "neoplastic" and "stage II" are displayed near the lesion region 61, and "neoplastic" and "stage I" are displayed near the lesion region 62.

In the example shown in FIG. 6, for the lesion regions 61 and 62, the category classifications relating to the lesion are the same, and the category classifications relating to the disease stage are different. However, in a case where the category classifications relating to the lesion of a plurality of lesion regions are different, there may be provided a category classification relating to the lesion of which the disease stage is the same or the classification by the disease stage is not provided.

[Medical Image Process]

FIG. 7 is a flowchart showing a medical image processing method according to an embodiment of the invention, and relates to a process procedure of each unit of the medical image processing device 14.

In FIG. 7, the medical image acquisition unit 40 acquires the medical image to be subjected to the recognition process, from the processor device 12 or the image storage unit 50. The acquired medical image is input to the first recognizer 41 (step S10).

The first recognizer 41 executes the recognition process of the medical image acquired in step S10 and acquires the recognition result (first recognition result) (step S12). The first recognizer 41 classifies the medical image into any category among the plurality of categories relating to the lesion (for example, "neoplastic", "non-neoplastic", and "others"), but the recognition result is output as three scores corresponding to "neoplastic", "non-neoplastic", and "others".

The recognition confidence level determination device 43 determines the confidence level for the category classification of the medical image specified by the recognition result, on the basis of the first recognition result (step S14). Specifically, the recognition confidence level determination device 43 inputs the first recognition result (in this example, three scores) by the first recognizer 41, and in a case where the difference between the highest score among the three scores and the other scores is equal to or greater than the reference value, the recognition confidence level determination device 43 classifies the image into a category having the highest score, and determines that the confidence level for the category classification is "high". Conversely, in a case where the difference between the scores of the categories is less than the reference value, the recognition confidence level determination device 43 classifies the image into a category having the highest score, and determines that the confidence level for the category classification is "low".

In step S14, in a case where it is determined that the confidence level for the first recognition result of the image by the first recognizer 41 is "low", the process proceeds to step S16.

In step S16, the second recognizer 42 with higher recognition accuracy than the first recognizer 41 is used, and the second recognizer 42 executes the recognition process of the medical image input in step S10, and acquires the recognition result (second recognition result).

Meanwhile, in step S14, in a case where it is determined that the confidence level for the first recognition result of the image by the first recognizer 41 is "high", the process proceeds to step S18.

In a case where it is determined that the confidence level for the first recognition result of the image by the first recognizer 41 is "high", the control unit 44 or the information display control unit 45B causes the display unit 16 to display the first recognition result in step S18. Meanwhile, in a case where it is determined that the confidence level for the first recognition result of the image by the first recognizer 41 is "low" and the second recognition result by the second recognizer 42 is acquired, the control unit 44 or the information display control unit 45B causes the display unit 16 to display the second recognition result instead of the first recognition result or together with the first recognition result, in step S18.

Subsequently, the control unit 44 determines whether to end the image process for the category classification of the medical image. In a case where the image process is not to be ended (in case of "No"), the process proceeds to step S10, and the control unit 44 repeatedly executes the processes from step S10 to step S20 for the next medical image to be subjected to the recognition process.

On the other hand, in a case where the image process is to be ended (in case of "Yes"), the control unit 44 ends the process in the medical image processing method. In a case where the recognition process for all of the medical images to be subjected to the recognition process is ended, the control unit 44 ends the image process.

[Others]

A case in which the CNNs having the layer structure with different number of layers are applied as the first recognizer 41 and the second recognizer 42 of the medical image processing device 14 of the embodiment has been described, but without being limited thereto, the recognition of the medical image may be performed by another method different from the CNN. For example, the first recognizer 41 may perform recognition of the medical image by another method different from the CNN, and the second recognizer 42 may perform recognition of the medical image by the CNN.

As another method for recognizing the medical image, for example, the medical image is divided into a plurality of rectangular regions, and each divided rectangular region is set as a local region. Then, it is considered that the feature quantity of the pixels in the local region is calculated for each local region of the medical image, a lesion candidate having a specific color, shape, or the like is extracted, the category classification of the medical image is performed by collating the image of the extracted lesion candidate (feature quantity of the image) with a reference lesion image (feature quantity of the lesion image) for each of category classifications prepared in advance.

In the above-described embodiment, the processor device 12 and the medical image processing device 14 are separately provided, but the processor device 12 and the medical image processing device 14 may be integrally provided. That is, the processor device 12 may have a function as the medical image processing device 14.

In the above-described embodiment, the medical image captured by the endoscope 10 is the recognition target for the category classification, but the medical image captured by an ultrasound diagnostic apparatus, an X-ray image diagnosis system, digital mammography, a computed tomography (CT) apparatus, a magnetic resonance imaging (MRI) apparatus, and the like may be used as the recognition target for the category classification.

[Additional Remark]

The present specification includes disclosure of various technical ideas including the inventions described below.

[Additional Remark A1]

A medical image processing device according to an embodiment of the invention further comprising: a medical image analysis processing unit that detects a notable region, which is a region to be noticed, on the basis of a feature quantity of pixels of a medical image, and a medical image analysis result acquisition unit that acquires an analysis result of the medical image analysis processing unit.

[Additional Remark A2]

A medical image processing device according to an embodiment of the invention further comprising: a medical image analysis processing unit that detects presence or absence of a target to be noticed, on the basis of a feature quantity of pixels of a medical image, and a medical image analysis result acquisition unit that acquires an analysis result of the medical image analysis processing unit.

[Additional Remark A3]

The medical image processing device according to Additional remark A1 or A2, wherein the medical image analysis result acquisition unit acquires the analysis result from a recording device recording an analysis result of the medical image, and the analysis result includes any one or both of the notable region that is the region to be noticed included in the medical image and presence or absence of the object to be noticed.

[Additional Remark B1]

The medical image processing device described in any one of Additional remarks A1 to A3, wherein the medical image is a normal light image that is obtained from the application of light in a white-light wavelength range or light in a plurality of wavelength ranges as the light in a white-light wavelength range.

[Additional Remark B2]

The medical image processing device according to Additional remark B 1, wherein the medical image is an image that is obtained from the application of light in a specific wavelength range, and the specific wavelength range is a range narrower than the white-light wavelength range.

[Additional Remark B3]

The medical image processing device according to Additional remark B2, wherein the specific wavelength range is a blue-light wavelength range or a green-light wavelength range of a visible-light wavelength range.

[Additional Remark B4]

The medical image processing device according to Additional remark B3, wherein the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

[Additional Remark B5]

The medical image processing device according to Additional remark B2, wherein the specific wavelength range is a red-light wavelength range of a visible-light wavelength range.

[Additional Remark B6]

The medical image processing device according to Additional remark B5, wherein the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

[Additional Remark B7]

The medical image processing device according to Additional remark B2, wherein the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin.

[Additional Remark B8]

The medical image processing device according to Additional remark B7, wherein the specific wavelength range includes a wavelength range of 400±10 nm, 440±10 nm, 470±10 nm, or 600 nm to 750 nm, and light in the specific wavelength range has a peak wavelength in a wavelength range of 400±10 nm, 440±10 nm, 470±10 nm, or 600 nm to 750 nm.

[Additional Remark B9]

The medical image processing device according to Additional remark B2, wherein the medical image is an in-vivo image of the inside of a living body, and the in-vivo image has information of fluorescence emitted by fluorescent materials.

[Additional Remark B10]

The medical image processing device according to Additional remark B9, wherein the fluorescence is obtained from the application of excitation light, which has a peak wavelength in a wavelength range of 390 nm to 470 nm, to the inside of the living body.

[Additional Remark B11]

The medical image processing device according to Additional remark B2, wherein the medical image is an in-vivo image of the inside of a living body, and the specific wavelength range is an infrared wavelength range.

[Additional Remark B12]

The medical image processing device according to Additional remark B11, wherein the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

[Additional Remark B13]

The medical image processing device described in any one of Additional remarks A1 to A3, wherein a medical image acquisition unit comprises a special light image acquisition unit that acquires a special light image including information about the specific wavelength range on the basis of a normal light image obtained from the application of light in a white-light wavelength range or light in a plurality of wavelength ranges as the light in a white-light wavelength range, and the medical image is the special light image.

[Additional Remark B14]

The medical image processing device according to Additional remark B13, wherein a signal in the specific wavelength range is obtained from an arithmetic operation based on color information about red, green, and blue or cyan, magenta, and yellow included in the normal light image.

[Additional Remark B15]

The medical image processing device described in any one of Additional remarks A1 to A3 further comprising: a feature-quantity-image generation unit generating a feature quantity image from an arithmetic operation based on at least one of the normal light image that is obtained from the application of light in a white-light wavelength range or light in a plurality of wavelength ranges as the light in a white-light wavelength range and the special light image that is obtained from the application of light in a specific wavelength range, the medical image is the feature quantity image.

[Additional Remark C1]

An endoscope device comprising: the medical image processing device described in any one of Additional remarks described above; and an endoscope that acquires an image from the application of at least one of light in a white-light wavelength range or light in the specific wavelength range.

[Additional Remark C2]

A diagnosis support apparatus comprising: the medical image processing device according to any one of Additional remarks described above.

[Additional Remark C3]

A medical service support apparatus comprising: the medical image processing device according to any one of Additional remarks described above.

EXPLANATION OF REFERENCES

9: endoscope system
10: endoscope
11: light source device
12: processor device
13: display device
14: medical image processing device
15: operation unit
16: display unit
17A, 17B, 17C: screen
18A, 18B, 18C: index
19: information
20: insertion part
21: hand operation part
22: universal cord
25: soft portion
26: bendable portion
27: distal end portion
28: image pick-up element
29: bendable operation knob
30: air/water supply button
31: suction button
32: static image capturing instruction portion
33: treatment tool inlet
35: light guide
36: signal cable
37A, 37B: connector
38: video
38a: frame image
39: static image
40: medical image acquisition unit
41: first recognizer
41A: input layer
41B: intermediate layer
41C: output layer
42: second recognizer
43: recognition confidence level determination device
44: control unit
45: display control unit
45A: image display control unit
45B: information display control unit
47: storage unit
50: image storage unit
51: program
61, 62: lesion region
S10 to S20: step

What is claimed is:

1. A medical image processing device comprising:
a processor configured to:
acquire a medical image including an image of a subject;
perform a first recognition of the medical image using a first recognizer;
determine a confidence level for a recognition result of the first recognition by the first recognizer; and
perform a second recognition of the medical image using a second recognizer according to the confidence level for the recognition result of the first recognition, the second recognizer having higher recognition accuracy than the first recognizer,
wherein each of the first recognizer and the second recognizer has a layer structure, and the number of layers constituting the layer structure of the second recognizer is greater than the number of layers constituting the layer structure of the first recognizer.

2. The medical image processing device according to claim 1,
wherein the first recognizer and the second recognizer have at least one filter in the layer constituting the layer structure.

3. The medical image processing device according to claim 1,
wherein each of the first recognizer and the second recognizer is a convolutional neural network.

4. The medical image processing device according to claim 1,
wherein each of the first recognizer and the second recognizer detects a position of a lesion candidate from the medical image.

5. The medical image processing device according to claim 1,
wherein each of the first recognizer and the second recognizer classifies the medical image into any category of a plurality of categories relating to a lesion.

6. The medical image processing device according to claim 1,
wherein each of the first recognizer and the second recognizer classifies a plurality of lesion regions on the medical image into any category of a plurality of categories relating to a lesion.

7. The medical image processing device according to claim 5,
wherein the plurality of categories are a plurality of categories relating to a type of a lesion, a plurality of categories relating to a disease stage of a lesion, or a plurality of categories in which a type and a disease stage of a lesion are combined.

8. The medical image processing device according to claim 1,
wherein the processor is further configured to cause a display to display a recognition result of the medical image by at least one of the first recognizer or the second recognizer.

9. The medical image processing device according to claim 8,
wherein in a case where the second recognizer is used for recognition of the medical image, the processor is configured to cause the display to display information indicating that the second recognizer is used.

10. The medical image processing device according to claim 8,
wherein in a case where the second recognizer is used for recognition of the medical image, the processor is configured to cause the display to display information indicating that the second recognition by the second recognizer is in progress for a period from the start to the end of the second recognition by the second recognizer.

11. The medical image processing device according to claim 1, further comprising:
a storage that records a recognition result of the medical image by at least one of the first recognizer or the second recognizer.

12. The medical image processing device according to claim 7,
wherein the processor is further configured to:
determine a confidence level for a category classification of the second recognition by the second recognizer;
cause the display to display a menu for a category selection of the medical image in a case where the confidence level for the category classification of second recognition is low, and
receive a selection of the category selection of the medical image.

13. The medical image processing device according to claim 12,
wherein the processor is further configured to decide a category priority of the plurality of categories on the basis of a category recognition result of the second recognition by the second recognizer, and changes a display order of the plurality of categories in the menu for the category selection according to the category priority.

14. The medical image processing device according to claim 12,
wherein in a case where the category of the medical image is decided, the processor is further configured to cause the display to display information indicating that the category of the medical image is decided.

15. A medical image processing method comprising:
acquiring a medical image including an image of a subject;
performing a first recognition of the medical image using a first recognizer;
determining a confidence level for a recognition result of the first recognition by the first recognizer; and
performing a second recognition of the medical image using a second recognizer according to the confidence level for the recognition result of the first recognition, the second recognizer having higher recognition accuracy than the first recognizer,
wherein each of the first recognizer and the second recognizer has a layer structure, and the number of layers constituting the layer structure of the second recognizer is greater than the number of layers constituting the layer structure of the first recognizer.

16. The medical image processing method according to claim 15,
wherein in a case where the confidence level for the recognition result of the first recognition is equal to or greater than a reference value, the recognition result of the first recognition is displayed on a display, and in a case where the confidence level for the recognition result of the first recognition is less than the reference value, the recognition result of the second recognition is displayed on the display.

17. A non-transitory computer readable medium for storing a medical image processing program causing a computer to execute a process comprising:
acquiring a medical image including an image of a subject;
performing a first recognition of the medical image using a first recognizer;
determining a confidence level for a recognition result of the first recognition by the first recognizer; and
performing a second recognition of the medical image using a second recognizer according to the confidence level for the recognition result of the first recognition, the second recognizer having higher recognition accuracy than the first recognizer,
wherein each of the first recognizer and the second recognizer has a layer structure, and the number of layers constituting the layer structure of the second recognizer is greater than the number of layers constituting the layer structure of the first recognizer.

18. The non-transitory computer readable medium for storing the medical image processing program according to claim 17,
  wherein in a case where the confidence level for the recognition result of the first recognition is equal to or greater than a reference value, the recognition result of the first recognition is displayed on a display, and in a case where the confidence level for the recognition result of the first recognition is less than the reference value, the recognition result of the second recognition is displayed on the display.

* * * * *